United States Patent [19]
Kaptein et al.

[11] Patent Number: 6,025,506
[45] Date of Patent: Feb. 15, 2000

[54] PROCESS FOR PREPARING AN OPTICALLY ACTIVE PHENYLGLYCIDYL ACID DERIVATIVE

[75] Inventors: Bernardus Kaptein, Sittard; Gerardus K. M. Verzijl, Bergen, both of Netherlands

[73] Assignee: DSM N.V., Netherlands

[21] Appl. No.: 09/027,619

[22] Filed: Feb. 23, 1998

Related U.S. Application Data

[60] Provisional application No. 60/051,675, Jul. 3, 1997.

[30] Foreign Application Priority Data

Feb. 21, 1997 [NL] Netherlands .......................... 1005338

[51] Int. Cl.$^7$ ...................... C07D 301/08; C07D 303/38
[52] U.S. Cl. ............................................. 549/519; 549/549
[58] Field of Search ...................... 549/519, 549

[56] References Cited

U.S. PATENT DOCUMENTS 5,008,433  4/1991  Palmer .

FOREIGN PATENT DOCUMENTS

342904 A2  11/1989  European Pat. Off. .

OTHER PUBLICATIONS

Schwartz et al., Enantioselective Synthesis of Calcium Channel Blockers of the Diltiazem Group. J. of Org. Chem. 57(3) 1992, pp. 851–856.

*Primary Examiner*—Johann Richter
*Assistant Examiner*—Taofiq A. Solola
*Attorney, Agent, or Firm*—Pillsbury Madison & Madison

[57] ABSTRACT

The invention relates to a process for preparing an optically active trans-compound having formula (1), in which R represents a phenyl group, whether or not substituted, preferably p-methoxyphenyl, and A is derived from an optically active compound, in which an aldehyde having formula (2), in which R is as defined above, is, in the presence of a base, brought into contact with an optically active acetyl compound having formula (3), in which X represents a leaving group and in which A is derived from an amino alcohol, preferably a β-amino alcohol having a rigid structure.

Particularly good results were obtained when use was made of a compound having formula (3), in which A is derived from an amino indanol compound having formula (4), in which $R_1$ and $R_2$ represent a (hetero)alkyl or (hetero)aryl group, whether or not substituted, having 1–10 C atoms, or $R_1$ and $R_2$ constitute an aromatic or aliphatic ring together with the N atom to which they are bound, in particular in which $R_1$ and $R_2$ each independently of one another represent methyl, ethyl, isopropyl, n-propyl, n-butyl, allyl, benzyl or tosyl.

19 Claims, No Drawings

PROCESS FOR PREPARING AN OPTICALLY ACTIVE PHENYLGLYCIDYL ACID DERIVATIVE

This application claims benefit of provisional application Ser. No. 60/051,675 filed Jul. 3, 1997.

FIELD OF THE INVENTION

The invention relates to a process for preparing an optically active trans-phenylglycidic acid derivative having formula (1),

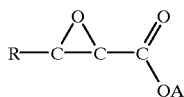
(1)

in which R represents a phenyl group, whether or not substituted, and A is derived from an optically active compound, in which an aldehyde having formula (2),

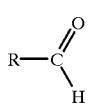
(2)

in which R is as defined above, is, in the presence of a base, brought into contact with an optically active acetyl compound having formula (3),

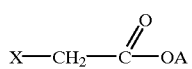
(3)

in which X represents a leaving group, characterized in that use is made of an optically active compound having formula (3) in which A is derived from an amino alcohol.

BACKGROUND INFORMATION

A similar process wherein an optically active trans-phenylglycidic derivate with formula (1) is prepared in which A represents (−)-8-phenylmenthyl chloroacetate is known from EP-A-342904.

SUMMARY AND OBJECTS OF THE INVENTION

The process according to the invention provides an alternative process wherein a high yield of the desired enantiomer and/or a high diastereomeric ratio can be obtained. Diastereoisomeric ratio means the (molar or weight) ratio between two diastereomeric isomers.

The invention relates to a process for preparing an optically active transcompound having formula (1), in which R represents a phenyl group, whether or not substituted, preferably p-methoxyphenyl, and A is derived from an optically active compound, in which an aldehyde having formula (2), in which R is as defined above, is, in the presence of a base, brought into contact with an optically active acetyl compound having formula (3), in which X represents a leaving group and in which A is derived from an amino alcohol, preferably a β-amino alcohol having a rigid structure.

Particularly good results were obtained when use was made of a compound having formula (3), in which A is derived from an amino indanol compound having formula (4), in which $R_1$ and $R_2$ represent a (hetero)alkyl or (hetero)aryl group, whether or not substituted, having 1–10 C atoms, or $R_1$ and $R_2$ constitute an aromatic or aliphatic ring together with the N atom to which they are bound, in particular in which $R_1$ and $R_2$ each independently of one another represent methyl, ethyl, isoprpyl, n-propyl, n-butyl, allyl, benzyl or tosyl.

DETAILED DESCRIPTION OF THE INVENTION

The aldehyde can be one having formula (2), in which R represents a phenyl group which may in one or more places be substituted with, for example, an alkyl group or an alkoxy group preferably having 1–20 C atoms, in particular 1–5 C atoms.

The acetyl compound can be a compound having formula (3), in which X represents a leaving group and A a chiral group derived from an optically active amino alcohol (AOH). Groups that can be used as the leaving group are commonly known from the literature. Very suitable leaving groups are for example halogenides, in particular Cl⁻ or Br⁻, sulphonates, for example p-toluene or methane sulphonate. Amino alcohols from which A may be derived are for example (salts of) a β-amino alcohol which preferably has a more or less rigid structure, for example because of the amino alcohol containing a ring structure. Particularly suitable examples of amino alcohols are substituted amino indanols having formula (4),

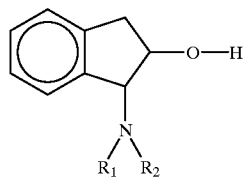
(4)

in which $R_1$ and $R_2$ represent a (hetero)alkyl, an alkenyl, a (hetero)aryl or an arylsulphonyl group, whether or not substituted, having 1–10 C atoms, or $R_1$ and $R_2$ constitute an aromatic or aliphatic ring together with the N atom to which they are bound. The best results were obtained when use was made of a haloacetyl compound having formula (3), in which X represents Cl and A is derived from an enantiomerically pure (i.e. having an enantiomeric excess (e.e.) >95%, in particular >99%) cis-amino indanol having formula (4), in which $R_1$ and $R_2$ are each independently methyl, ethyl, isopropyl, n-propyl, n-butyl, allyl, benzyl or tosyl.

Preferably a non-nucleophilic base is used as the base, for example a hydride, in particular potassium hydride or sodium hydride; an alkyl lithium, more in particular n-butyl lithium, or an alkoxide, preferably potassium t-butoxide. Preferably use is made of potassium t-butoxide.

As the solvent, use is made of for example chlorinated hydrocarbons, aromatic hydrocarbons or ethers that are inert in the reaction system, for example dichloromethane, toluene, xylene or tetrahydrofuran (THF). Preferably use is made of toluene or dichloromethane.

The temperature at which the reaction is carried out is not particularly critical and preferably lies between −30 and 50° C., in particular between 10 and 40° C.

The molar ratio of the aldehyde and the acetyl compound is not critical either, and in practice preferably lies between 1:2 and 2:1, in particular between 1:1.1 and 1.1:1, with a virtually equimolar ratio seeming optimum.

Preferably use is made of a slight excess of base relative to the acetyl compound, for example a base:acetyl compound molar ratio of between 1:1 and 1.5:1, preferably between 1:1 and 1.1:1. It will be clear that when A is derived from a salt of an optically active amino alcohol, for example the HCl salt, an extra equivalent of the base will need to be used.

Optically active phenylglycidyl acid derivatives obtained with the process according to the invention can be used with particular advantage in the preparation of pharmaceuticals, in particular benzothiazepines, for example diltiazem and clenthiazem. The invention also relates to optically active phenylglycidyl acid derivatives having formula (1) and to the use thereof in the preparation of such pharmaceuticals.

In particular, the invention also relates to the new optically active compounds having formula (1) in which R represents a phenyl group, whether or not substituted, as defined above and A is derived from an optically active cis-amino indanol (AOH) according to formula (4), in which $R_1$ and $R_2$ represent a (hetero)alkyl, an alkenyl, a (hetero) aryl or an arylsulphonyl group, whether or not substituted, having 1–10 C atoms, or $R_1$ and $R_2$ constitute an aromatic or aliphatic ring together with the N atom to which they are bound, $R_1$ and $R_2$ each independently preferably representing methyl, ethyl, isopropyl, n-propyl, n-butyl, allyl, benzyl or tosyl; and to the optically active acetyl compounds having formula (3), in which X represents a leaving group and A is as defined above.

The optically active compounds having formula (1) can be used as such directly in the preparation of pharmaceuticals or they can first be converted into a corresponding phenylglycidyl ester, for example the methyl, ethyl or t-butyl ester, for instance by reaction with a base and an alcohol e.g. an alkalimetal alkoxide with the desired ester corresponding alcohol as solvent. These phenylglycidyl esters can in turn be converted into pharmaceuticals in a known manner, for example through coupling with an optionally substituted 2-amino thiophenol and cyclisation to a benzothiazepine. Such benzothiazepines are intermediates in the preparation of known pharmaceuticals, for example diltiazem and clenthiazem. For the preparation of diltiazem use is made of for example the (2R,3S) compound having formula (1), in which R represents p-methoxyphenyl and A is derived from (1S, 2R)-amino indanol, or a corresponding p-methoxyphenylglycidyl ester obtained therefrom is first brought into contact with for example a 2-amino thiophenol, after which the reaction product obtained is subjected to a cyclisation reaction, optionally followed by an alkylation and acylation reaction.

The invention will now be further elucidated with reference to the examples, without being limited thereto.

EXAMPLES

Example I
(1S,2R)-1-(Diethylamino)-2-indanol

A suspension of 15.09 grams (101 mmol) of (1S,2R)-1-amino-2-indanol, 33.72 grams (244 mmol) of potassium carbonate and 38.8 grams (249 mmol) of ethyl iodide in 100 ml of acetonitrile was refluxed for 3 hours. After cooling, the solid matter was removed through filtration and the filtrate was evaporated. The residue was dissolved in 4N hydrochloric acid and was washed three times using dichloromethane. The water layer was made basic with the aid of a 50% sodium hydroxide solution and was extracted with the aid of dichloromethane (3*25 ml). After drying ($Na_2SO_4$) and evaporation, the product was isolated as an oil. This oil was dissolved in diethyl ether and cooled, which caused the product to crystallise. Yield: 16.7 grams (81%) of a white solid substance. Melting point: 60–61° C. $[\alpha]^{20}_D$+1.1 (c=1, methanol). $^1$H NMR (200 MHz, $CDCl_3$): 1.02 (t, 6H), 2.24–2.57 (2*m, 4H), 2.65 (dd, 1H), 3.20 (dd, 1H), 4.22 (d, 1H), 4.29 (q, 1H), 4.7 (br s, 1H) and 7.10–7.27 (m, 4H). $^{13}$C NMR (50.31 MHz, $CDCl_3$): 13.63 (q), 41.42 (t), 45.60 (t) 66.97 (d), 68.95 (d), 125.44 (d), 126.17 (d), 126.45 (d), 128.28 (d), 139.65(s) and 141.98 (s).

Example II
(1S,2R)-N-Methyl,N-i-propyl-1-amino-2-indanol

A solution of 4.0 grams of (1S,2R)-1-(i-propylamino)-2-indanol (20.9 mmol), 30 ml of formic acid and 15 g of Formalin was refluxed for 24 hours. After cooling, the reaction mixture was evaporated and dissolved in 50 ml of an aqueous 4N sodium hydroxide solution. The basic solution was extracted with the aid of dichloromethane (2*50 ml). After drying ($Na_2SO_4$) and evaporation, the oil was chromatographed using silica gel 60 (eluant: ethylacetate/petroleum ether (40–70) 3:1).

Yield: 3.4 grams (79%) of a colourless oil. $[\alpha]^{20}_D$+8.6 (c=1, methanol). $^1$H NMR (200 MHz, $CDCl_3$): 0.95 (d, 6H) 1.67 (s, 3H), 2.48 (dd, J=8.3 and 3.5 Hz, 1H), 2.83 (septet, 1H), 3.02 (dd, J=8.3 and 3.9 Hz, 1H), 3.98–4.12 (m, 2H), 4.9 (br s, 1H) and 6.94–7.08 (m, 4H). $^{13}$C NMR (50.31 MHz, $CDCl_3$): 21.40 (q), 21.76 (q), 35.67 (q), 42.86 (t), 56.51 (d), 66.70 (d), 70.70 (d), 126.99 (d), 127.81 (d), 128.40 (d), 129.66 (d), 140.63 (s) and 143.67 (s).

Example III
(1S,2R)-1-(Diethylamino)-2-indanyl chloroacetate 1.70 grams (17 mmol) of chloroacetyl chloride was added, drop by drop, in 5 minutes, to a solution of 2.65 grams (13 mmol) of (1S,2R)-1-(diethylamino)-2-indanol in 40 ml of dichloromethane at room temperature. The temperature increased to 30° C. The reaction was stirred for 15 hours at room temperature. After evaporation of the solution, 4.15 grams (91%) of HCl salt was obtained as a yellow foam. $^1$H NMR (200 MHz, $CDCl_3$): 1.27 (t, 3H), 1.49 (t, 3H), 2.80 (septet, 1H), 2.96–3.39 (m, 5H), 4.16 (d, J=7.8 Hz, 1H), 4.41 (d, J=7.8 Hz, 1H), 5.04 (br d, 1H), 5.78 (q, 1H), 7.15–7.37 (m, 3H), 7.55 (d, 1H) and 11.5 (br s, 1H). The HCl salt can be quantitatively liberated to yield a colourless oil through extraction using a dichloromethane/5% $K_2CO_3$ solution in water. $^1$H NMR (200 MHz, $CDCl_3$): 0.97 (t, 6H), 2.40–2.71 (m, 4H), 2.93 (dd, 1H), 3.12 (dd, 1H), 3.96 (s, 2H), 4.50 (d,1H), 5.56 (ddd, 1H) and 7.15–7.30 (m, 4H). $^{13}$C NMR (50.31 MHz, $CDCl_3$): 14.74 (q), 37.51 (t), 41.25 (t), 45.25 (t), 66.64 (d), 77.89 (d), 124.92 (d), 125.26 (d), 126.89 (d), 127.76 (d), 139.07 (s), 141.20 (s) and 167.03 (s).

Example IV
(1S,2R)-N-Methyl,N-i-propyl-1-amino-2-indanyl chloroacetate 2.00 grams (17.5 mmol) of chloroacetyl chloride was added drop by drop, in 5 minutes, to a solution of 3.00 grams (14.6 mmol) of (1S,2R)-N-methyl,N-i-propyl-1-amino-2-indanol in 40 ml of dichloromethane at room temperature. The temperature increased to 35° C. The reaction was stirred for 15 hours at room temperature. This was followed by the addition of 50 ml of a 5% $K_2CO_3$ solution in water and extraction. The basic water layer was once again extracted using 30 ml of dichloromethane. After the collected organic layers had been washed with water, dried using $Na_2SO_4$ and evaporated, 3.96 grams (85%) of product was isolated as a yellow oil. $^1$H NMR (200 MHz, $CDCl_3$): 1.05 (2*d, 6H), 2.09 (s, 3H), 2.96 (dd, J=8.6 and 3.5 Hz +septet, 2H), 3.14 (dd, J=8.6 and 3.5 Hz, 1H), 3.99 (s, 2H), 4.47 (d, J=3,1 Hz, 1H), 5.47 (dt, J=3,1 and 3.5 Hz, 1H) and 7.10–7.25 (m, 4H). $^{13}$C NMR (50.31 MHz, CDCl$_3$): 20.59 (q), 33.00 (q), 37.06 (t), 41.10 (t), 53.61 (d), 66.08 (d), 78.47 (d), 124.84 (d), 125.81 (d), 126.62 (d), 127.61 (d), 138.96 (s), 140.46 (s) and 166.85 (s).

Example V (2R,3S)-3-(4-Methoxyphenyl)oxirane-2-carboxylic (1S,2R)-1-(diethylamino)-2-indanyl ester In 5–10 min., 0.95 grams (8.5 mmol) of potassium tert-butoxide was added, in small portions, to a solution of 2.05 grams (7.3 mmol) of (1S,2R)-1-(diethylamino)-2-indanyl chloroacetate and 1.0 gram (7.3 mmol) of p-anisic aldehyde in 40 ml of toluene at 20° C. The temperature increased to 25° C. After 30 minutes' stirring the reaction was quenched using a diluted NaHCO$_3$ solution in water. The organic layer was separated and washed with water, dried using Na$_2$SO$_4$ and evaporated. Yield: 2.75 grams (90%) of a yellow oil. This oil is a mixture of (2R,3S)-3-(4-methoxyphenyl)oxirane-2-carboxylic (1S,2R)-1-(diethylamino)-2-indanyl ester (diastereomeric ratio 89:11) and (2R,3S)-3-(4-methoxyphenyl)oxirane-2-carboxylic tert-butyl ester (enantiomeric excess 80%). $^1$H NMR (200 MHz, CDCl$_3$): 1.02 (2*t, 6H), 2.48–2.78 (m,4H), 2.95–3.27 (m, 2H), 3.44 (d, J=2.0 Hz) and 3.48 (d, J=2.0 Hz, together 1H for major and minor diastereomers, resp.), 3.80 (s, 3H), 4.02 (d, J=2.0 Hz) and 4.07 (d, J=2.0 Hz, together 1H for minor and major diastereomers, resp.), 4.60 (d, 1H), 5.62–5.75 (m, 1H), 6.85 (d, 2H) and 7.15–7.38 (d+m, 6H). $^{13}$C NMR (50.31 MHz, CDCl$_3$): 14.71 (q), 37.58 (t), 45.35 (t), 55.30 (q), 56.85 (d), 57.97 (d), 66.51 (d), 77.02 (d), 113.49 (d), 114.10 (d), 124.93 (d), 125.32 (d), 126.81 (d), 127.12 (d), 127.27 (d), 127.74 (s), 139.16 (s), 160.18 (s) and 168.16 (s). (2R,3S)-3-(4-methoxyphenyl)oxirane-2-carboxylic tert-butyl ester: $^1$H NMR (200 MHz, CDCl$_3$): 1.43 (s, 9H), 3.33 (d, 1H), 3.73 (s, 3H), 3.89 (d, 3H), 6.81 (d, 2H) and 7.14 (d, 2H).

Example VI (2R,3S)-3-(4-Methoxyzenyl)oxirane-2-carboxylic (1S,2R)-1-(diethylamino)-2-indanyl ester In 5–10 min., 3.50 grams (31 mmol) of potassium tert-butoxide was added, in small portions, to a solution of 4.9 grams (12.5 mmol) of (1S,2R)-1-(diethylamino)-2-indanyl chloroacetate HCl salt and 1.70 grams (12.5 mmol) of p-anisic aldehyde in 50 ml of dichloromethane at 20° C. The temperature increased to 30° C. After 60 minutes' stirring the reaction was quenched using a 0.5M KH$_2$PO$_4$ solution in water. The organic layer was separated and washed with water, dried using Na$_2$SO$_4$ and evaporated. Yield: 5.10 grams (99%) of a brown oil (a mixture of (2R,3S)-3-(4-methoxyphenyl)oxirane-2-carboxylic (1S,2R)-1-(diethylamino)-2-indanyl ester (diastereomeric ratio 89:11) and (2R,3S)-3-(4-methoxyphenyl)oxirane-2-carboxylic tert-butyl ester (enantiomeric excess 75%)).

Example VII (2R,3S)-3-(4-Methoxyphenyl)oxirane-2-carboxylic (1S,2R)-N-methyl,N-i-propyl-1-amino-2-indanyl ester In 5 min., 1.50 grams (13.4 mmol) of potassium tert-butoxide was added, in small portions, to a solution of 3.82 grams (12.0 mmol) of (1S,2R)-N-methyl,N-i-propyl-1-amino-2-indanyl chloroacetate and 1.63 grams (12.0 mmol) of p-anisic aldehyde in 50 ml of toluene at 20° C. The temperature increased to 33° C. After 30 minutes' stirring the reaction was quenched with the aid of a 1M NaHCO$_3$ solution in water. The organic layer was separated and washed with water, dried with the aid of Na$_2$SO$_4$ and evaporated. Yield: 4.90 grams (98%) of a yellow oil (a 77:23 mixture of (2R,3S)-3-(4-methoxyphenyl)oxirane-2-carboxylic (1S,2R)-N-methyl,N-i-propyl-1-amino-2-indanyl ester (diastereomeric ratio 79:21) and (2R,3S)-3-(4-methoxyphenyl)oxirane-2-carboxylic tert-butyl ester). $^1$H NMR (200 MHz, CDCl$_3$): 1.12 (2*d, 6H), 2.21 (s, 3H), 3.05–3.38 (m, 3H), 3.52 (d, J=2.0 Hz, 0.95H), 3.56 (d, J=2.0 Hz, 0.05H), 3.79 (s, 3H), 4.05 (d, J=2.0 Hz, 1H), 4.60 (d, 1H), 5.63 (m, 1H), 6.91 (d, 2H) and 7.18–7.37 (d+m, 6H). $^{13}$C NMR (50.31 MHz, CDCl$_3$): 20.53 (q), 20.80 (q), 33.35 (q), 37.17 (t), 53.34 (d), 55.23 (q), 56.76 (d), 57.83 (d), 66.22 (d), 78.16 (d), 114.02 (d), 124.89 (d), 125.81 (d), 126.62 (d), 127.02 (d), 127.56 (d), 127.91 (s), 139.06 (s), 141.0 (s), 160.08 (s) and 167.90 (s).

Example VIII (2S,3S)-2.3-Dihydro-3-hydroxy-2-(4-methoxyphenyl)-1,5-benzothiazepin-4(5H)-on 2.0 grams (4.8 mmol) of the mixture of (2R,3S)-3-(4-methoxyphenyl)oxirane-2-carboxylic (1S,2R)-1-(diethylamino)-2-indanyl ester (diastereomeric ratio 89:11) and (2R,3S)-3-(4-methoxyphenyl)oxirane-2-carboxylic tert-butyl ester (enantiomeric excess 80%) of Example V was dissolved in 20 ml of xylene+1 ml of methanol. This solution was heated to 120° C. and 600 mg (5.0 mmol) of 2-aminothiophenol was added drop by drop in 5 min. After 6 hours' heating at 120° C. the solution was cooled to 20° C. and 1.1 grams (6,0 mmol) of p-toluene sulphonic monohydrate was added. This was followed by 6 hours' heating at reflux temperature, during which 1–2 ml of a xylene/methanol mixture was removed through distillation. After cooling, the brown solution was dissolved in dichloromethane and washed with a 5% Na$_2$CO$_3$ solution in water and a 0.5M KH$_2$PO$_4$ solution in water. After drying with the aid of Na$_2$SO$_4$ and evaporation, the chemically pure product was obtained after chromatography using silica gel (eluant:toluene/ethyl acetate 2:1). 85% enantiomeric excess (determined with the aid of anisochrony in $^1$H NMR, see C. Giordano et al.; J. Org. Chem. 1991, (59), 2270). The enantiomeric excess was increased to >95% through one recrystallisation from toluene. White needles. Melting point: 200–202° C. $[\alpha]^{20}_D$+109 (c=0.4, methanol). $^1$H NMR (200 MHz, CDCl$_3$): 2.93 (d, 1H), 3.71 (s, 3H), 4.41 (dd, 1H), 5.02 (d, 1H), 6.74 (d, 2H), 7.03–7.21 (m, 2H), 7.29–7.44 (d+m, 3H), 7.61 (d, 1H) and 8.47 (br s, 1H). The (1S,2R)-1-(diethylamino)-2-indanol was recovered from the 0.5M KH$_2$PO$_4$ extraction solution.

Example IX (2R,3S)-3-(4-Methoxyphenyl)oxirane-2-carboxylic methyl ester

A solution of 2.5 grams (6.3 mmol) of the reaction product of Example VII in 15 ml of 0.35M sodium methoxide in methanol was stirred at room temperature for 1 hour. The solution was neutralised with the aid of 40 ml of a 0.5M KH$_2$PO$_4$ solution in water and was extracted with 2*30 ml chloroform. The chloroform solution was washed with 2*30 ml of a 0.5M KH$_2$PO$_4$ solution in water. After drying (Na$_2$SO$_4$) and evaporation, 1.24 grams (95%) of (2R,3S)-3-(4-methoxyphenyl)oxirane-2-carboxylic methyl ester was obtained. Enantiomeric excess 55%. $^1$H NMR (200 MHz, CDCl$_3$): 3.47 (d, 1H), 3.73 (s) and 3.76 (s, together 6H), 4.01 (d, 1H), 6.85 (d, 1H) and 7.18 (d, 2H). $^{13}$C NMR (50.31 MHz, CDCl$_3$) 52.00 (q), 54.78 (q), 55.99 (d) 57.40 (d), 113.59 (d), 126.17 (s), 126.66 (d), 159.73 (s) and 168.28 (s).

After neutralisation with the aid of a 50% sodium hydroxide solution in water and extraction with the aid of chloroform, 1.30 grams (100%) of (1S,2R)-N-methyl,N-i-propyl-1-amino-2-indanol was recovered from the acid water layers.

What we claim is:

1. A process for preparing an optically active trans-phenylglycidic acid derivative represented by formula (1),

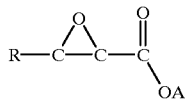
(1)

wherein R represents a phenyl group, whether or not substituted, and A is a residue of an enantiomerically pure amino indanol represented by the formula (4)

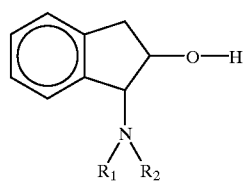
(4)

wherein $R_1$ and $R_2$ are each indenendently selected from the group consisting of methyl, ethyl, isopropyl, n-propyl, n-butyl, allyl, benzyl and tosyl, comprising:

contacting an aldehyde represented by formula (2),

(2)

wherein R is as defined above, in the presence of a base, with an optically active acetyl compound represented by formula (3),

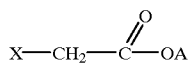
(3)

wherein X represents a chlorine atom as a leaving group.

2. A process according to claim 1, wherein R represents a p-methoxyphenyl group.

3. A process for preparing an optically active trans-phenylglycidic acid derivative represented by formula (1)

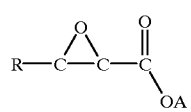
(1)

wherein R represents a phenyl group, whether or not substituted, and A represents a residue derived from an optically active amino indanol compound represented by the formula (4)

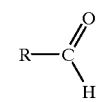
(4)

wherein $R_1$ and $R_2$ independently represent a (hetero)alkyl, an alkenyl or (hetero)aryl group, whether or not substituted, having 1–10 C atoms, or an arylsulphonyl group, or $R_1$ and $R_2$ constitute an aromatic or aliphatic ring together with the N atoms to which they are bound comprising:

contacting an aldehyde represented by formula (2),

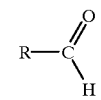
(2)

wherein R is as defined above, in the presence of a base, with an optically active acetyl compound represented by formula (3),

(3)

wherein X represents a leaving group.

4. A process according to claim 3, wherein $R_1$ and $R_2$ each independently of one another represent an alkyl or an alkenyl group having 1–4 C-atoms, a benzyl or a tosyl group.

5. Process according to any one of claims 1, 2, 3 or 4 in which potassium t-butoxide is used as the base.

6. A process according to claim 1, wherein R represents a phenyl group which has at least one substituent selected from the group consisting of alkyl groups having 1–20 carbon atoms and alkoxy groups having 1–20 carbon atoms.

7. A process according to claim 6, wherein said at least one substituent has 1–5 carbon atoms.

8. A process according to claim 1 or 3, wherein the process is conducted in a solvent selected from the group consisting of dichloromethane, toluene, xylene and tetrahydrofuran.

9. A process according to claim 3, wherein X represents a leaving group selected from halogenides and sulphonates.

10. The process according to claim 3, wherein R represents p-methoxyphenyl.

11. A process for preparing a compound comprising:

(a) contacting an aldehyde represented by formula (2), (2)

wherein R represents a phenyl group, whether or not substituted, in the presence of a base, with an optically active acetyl compound represented by formula (3),

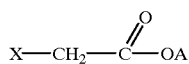  (3)

wherein X represents a leaving group, and A represents a residue from an optically active amino indanol compound represented by the formula (4)

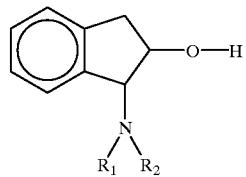  (4)

wherein $R_1$ and $R_2$ independently represent a (hetero)alkyl, an alkenyl or (hetero)aryl group, whether or not substituted, having 1–10 C atoms, or an arylsulphonyl group, or $R_1$ and $R_2$ constitute an aromatic or aliphatic ring together with the N atoms to which they are bound, wherein an optically active trans-phenylglycidic acid derivative represented by formula (1)

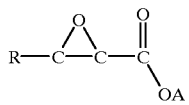  (1)

wherein R is as defined above, and A is as defined above is obtained;

(b) subjecting the derivative represented by formula (1) to a reaction with a base and an alcohol to produce the corresponding glycidylester.

12. A process for preparing a compound comprising:

(a) contacting an aldehyde represented by formula (2),

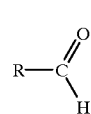  (2)

wherein R represents a phenyl group, whether or not substituted, in the presence of a base, with an optically active acetyl compound represented by formula (3),

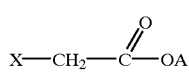  (3)

wherein X represents a chlorine atom as a leaving group, and A represents a residue of an enantiomerically pure amino indanol compound represented by the formula (4)

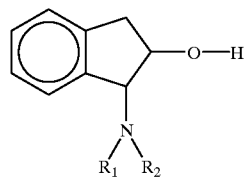  (4)

wherein $R_1$ and $R_2$ are each independently selected from the group consisting of methyl, ethyl, isoprpopyl, n-propyl, n-butyl, allyl, benzyl and tosyl, wherein an optically active trans-phenylglycidic acid derivative represented by formula (1)

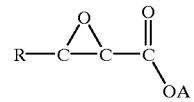  (1)

wherein R is as defined above, and A is as defined above is obtained; and (b) subjecting the derivative represented by formula (1) to a reaction with a base and an alcohol to produce the corresponding glycidylester.

13. The process according to claim 11 or 12, wherein the process further comprises (c) reacting the product obtained with at least one aminothiophenol.

14. The process according to claim 13, wherein the process further comprises (d) cyclizing the product obtained to obtain a benzothiazopine.

15. The process according to claim 14, wherein the cyclized product obtained os subsrquently alkylated or acylated.

16. The process according to claim 15, wherein the product obtained comprises diltiazem.

17. A process for making a compound comprising:

contacting an aldehyde represented by formula (2)

  (2)

wherein R represents a phenyl group, whether or not substituted, in the presence of a base, with an optically active acetyl compound represented by formula (3),

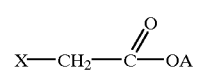  (3)

wherein X represents a leaving group, and A represents a residue from an optically active amino indanol compound represented by the formula (4)

(4)

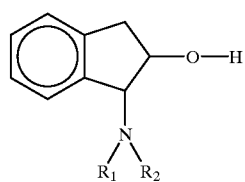

wherein $R_1$ and $R_2$ independently represent a (hetero)alkyl, an alkenyl or (hetero)aryl group, whether or not substituted, having 1–10 C atoms, or an arylsulphonyl group, or $R_1$ and $R_2$ constitute an aromatic or aliphatic ring together with the N atoms to which they are bound, wherein an optically active trans-phenylglycidic acid derivative represented by formula (1)

(1)

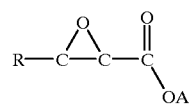

wherein R is as defined above, and A is as defined above is obtained; and subsequently subjecting a compound represented by formula (1) to a reaction with an aminothiophenol to "produce an intermediate and subsequently cyclizing the intermediate to obtain a benzothiazopine".

18. A process for making a compound comprising:
contacting an aldehyde represented by formula (2)

(2)

wherein R represents a phenyl group, whether or not substituted, in the presence of a base, with an optically active acetyl compound represented by formula (3), (3)

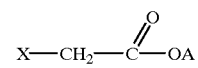

wherein X represents a chlorine atom as a leaving group, and A represents a residue from an optically active amino indanol compound represented by the formula (4)

(4)

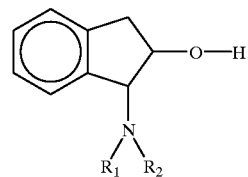

wherein $R_1$ and $R_2$ are each independently selected from the group consisting of methyl, ethyl, isopropyl, n-propyl, n-butyl, allyl, benzyl and tosyl, wherein an optically active trans-phenylglycidic acid derivative represented by formula (1)

(1)

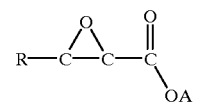

wherein R is as defined above, and A is as defined above is obtained; and subsequently subjecting a compound represented by formula (1) to a reaction with an aminothiophenol to produce an intermediate and subsequently cyclizing the intermediate to obtain a benzothiazopine.

19. The process according to claim 17 or 18, wherein the product obtained is subsequently alkylated or acylated.

* * * * *